United States Patent [19]
Martens et al.

[11] Patent Number: 5,753,196
[45] Date of Patent: May 19, 1998

[54] PLASMA WATER VAPOR STERILIZER APPARATUS

[75] Inventors: Phillip A. Martens, Fremont, Calif.; David L. Rainwater, Madison, Wis.

[73] Assignee: AbTox, Inc., Mundelein, Ill.

[21] Appl. No.: 739,032

[22] Filed: Oct. 28, 1996

Related U.S. Application Data

[62] Division of Ser. No. 491,170, Jun. 6, 1995, Pat. No. 5,603,895.

[51] Int. Cl.$^6$ ................... A61L 2/00; A61L 9/00
[52] U.S. Cl. .................. 422/293; 422/186; 422/292; 422/305; 422/307; 422/906
[58] Field of Search .................. 422/21, 22, 23, 422/28, 26, 27, 186, 186.05, 292, 293, 305, 307, 906; 588/227

[56] References Cited

U.S. PATENT DOCUMENTS

| | | |
|---|---|---|
| 3,701,628 | 10/1972 | Ashman . |
| 3,948,601 | 4/1976 | Fraser et al. . |
| 4,643,876 | 2/1987 | Jacobs et al. . |
| 5,084,239 | 1/1992 | Moulton et al. . |
| 5,115,166 | 5/1992 | Campbell et al. . |
| 5,171,525 | 12/1992 | Jacob . |
| 5,184,046 | 2/1993 | Campbell . |
| 5,244,629 | 9/1993 | Caputo et al. . |
| 5,413,759 | 5/1995 | Campbell et al. . |
| 5,451,368 | 9/1995 | Jacob . |
| 5,633,424 | 5/1997 | Graves et al. ............ 588/227 |

FOREIGN PATENT DOCUMENTS

| | | |
|---|---|---|
| 474137 | 3/1992 | European Pat. Off. . |
| 2253144 | 9/1992 | United Kingdom . |
| 9215336 | 9/1992 | WIPO . |

OTHER PUBLICATIONS

Premarket Notification (510(k)) of Johnson & Johnson, Oct. 1993, letter dated Dec. 11, 1991 to the FDA from Johnson & Johnson with Table of Contents; pp. 001 00002–00003, 002 00002–00013, 002 00018, 002 00022–00025, 002 00029–00042, 002 00046–00049, 002 00051–00052, 002 00056–00058, 002 00060, 002 00063–00064, 002 00069, 002 00075, and 002 00077–00078.

*Primary Examiner*—Krisanne Thornton
*Attorney, Agent, or Firm*—Majestic, Parsons, Siebert & Hsue

[57] ABSTRACT

An apparatus for plasma sterilization of articles includes a plasma generator, a sterilizing chamber, and a source of water vapor in fluid communication with the plasma generator, and may optionally include an autoclave. A method for plasma sterilization comprises exposing an article to be sterilized to a neutral active species of a plasma generated from water vapor. The exposure of the article to the plasma is carried out at reduced pressures and a chamber temperature of less than about 82° C. for a time period sufficient to effect sterilization.

3 Claims, 5 Drawing Sheets

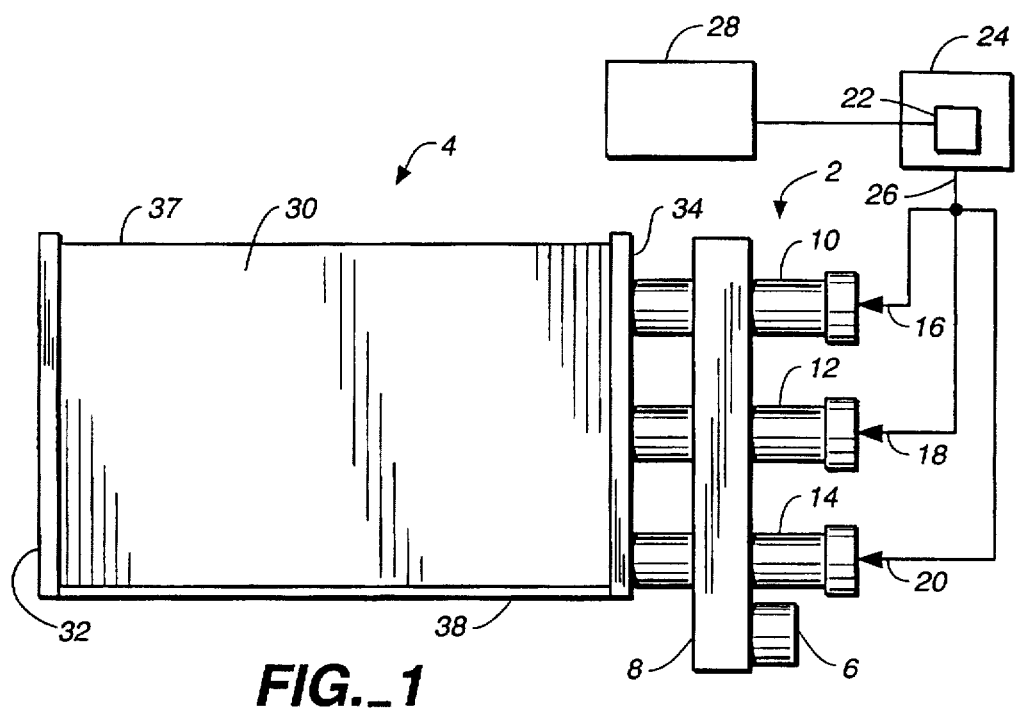
FIG._1
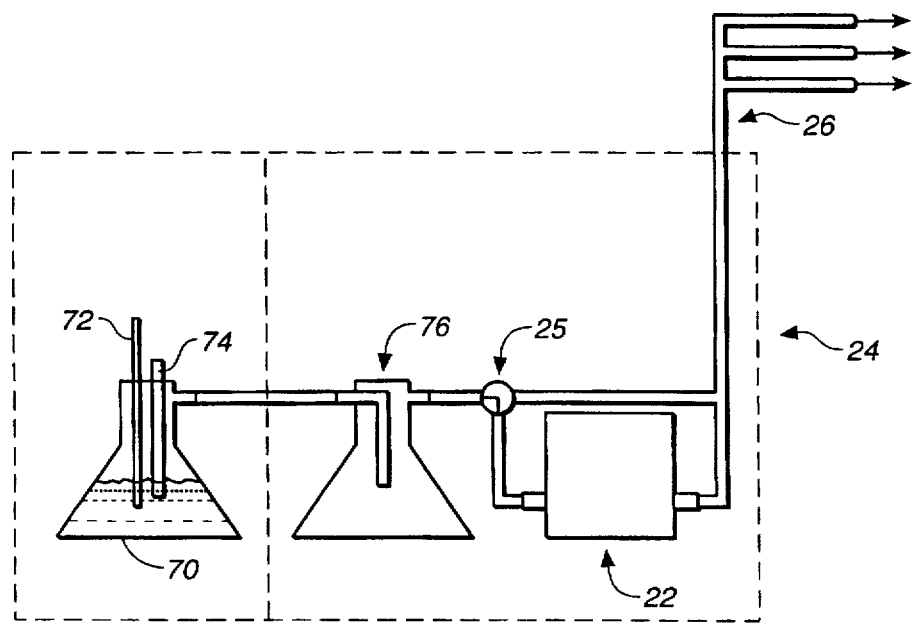
FIG._3

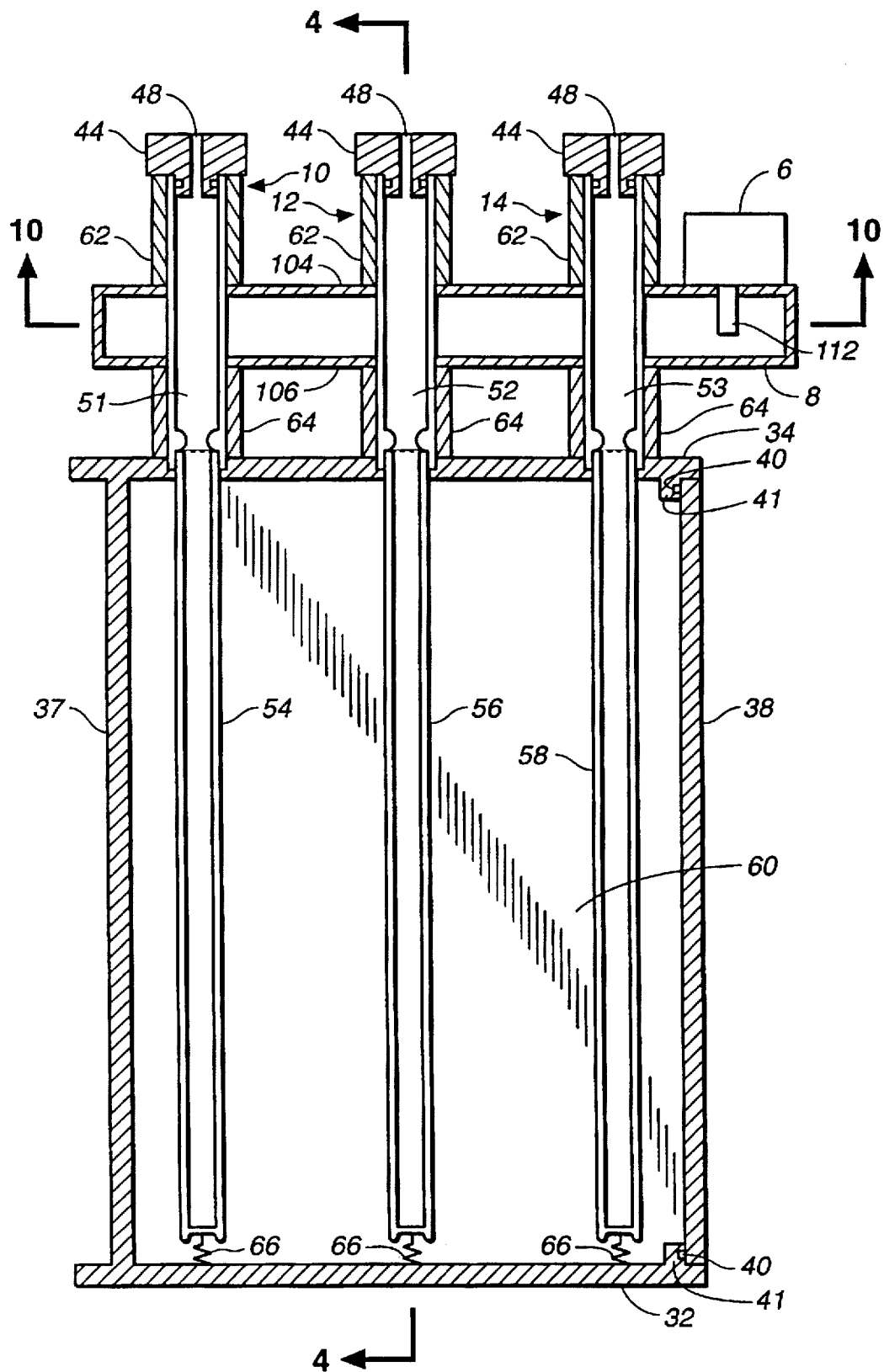
FIG._2

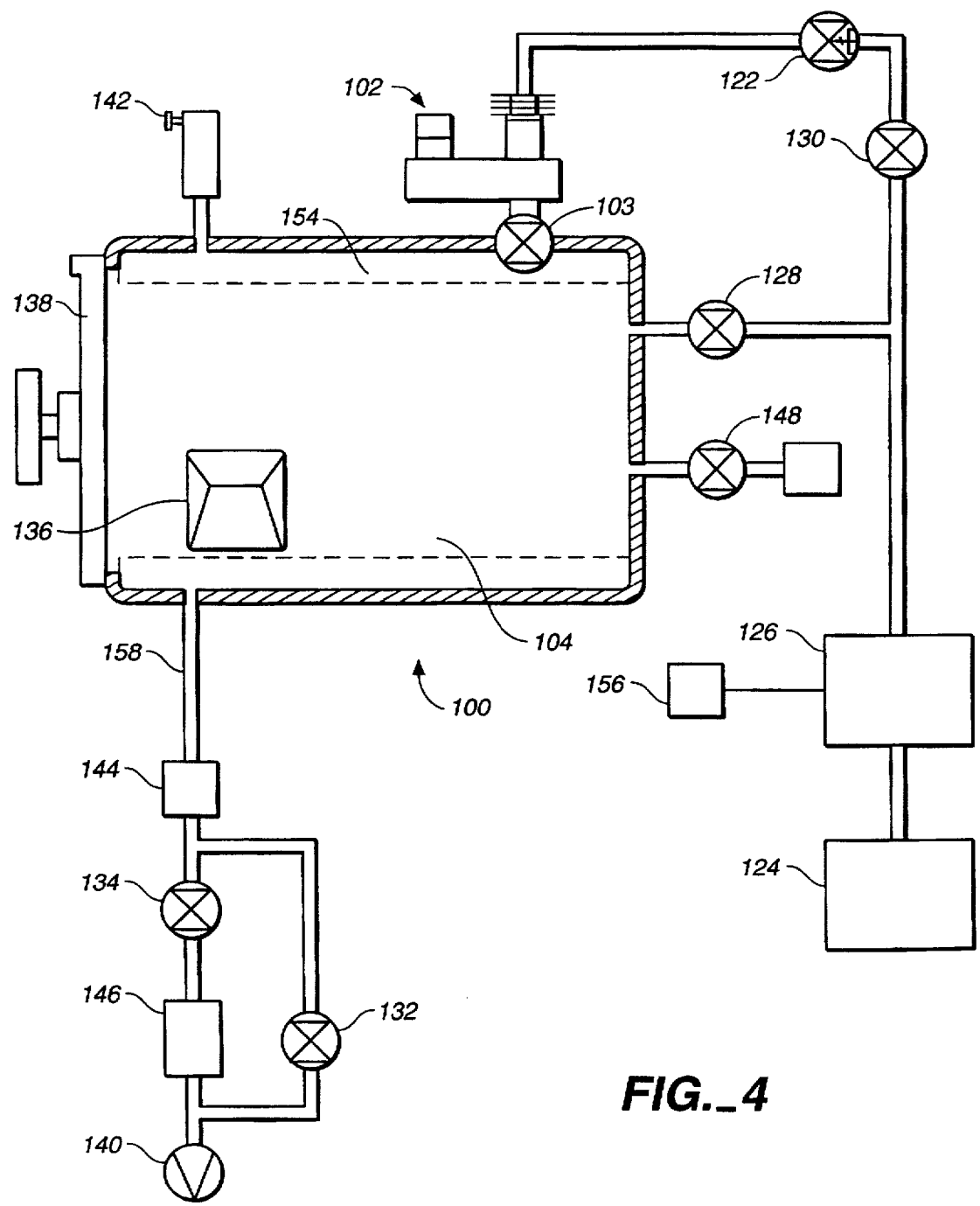
FIG._4

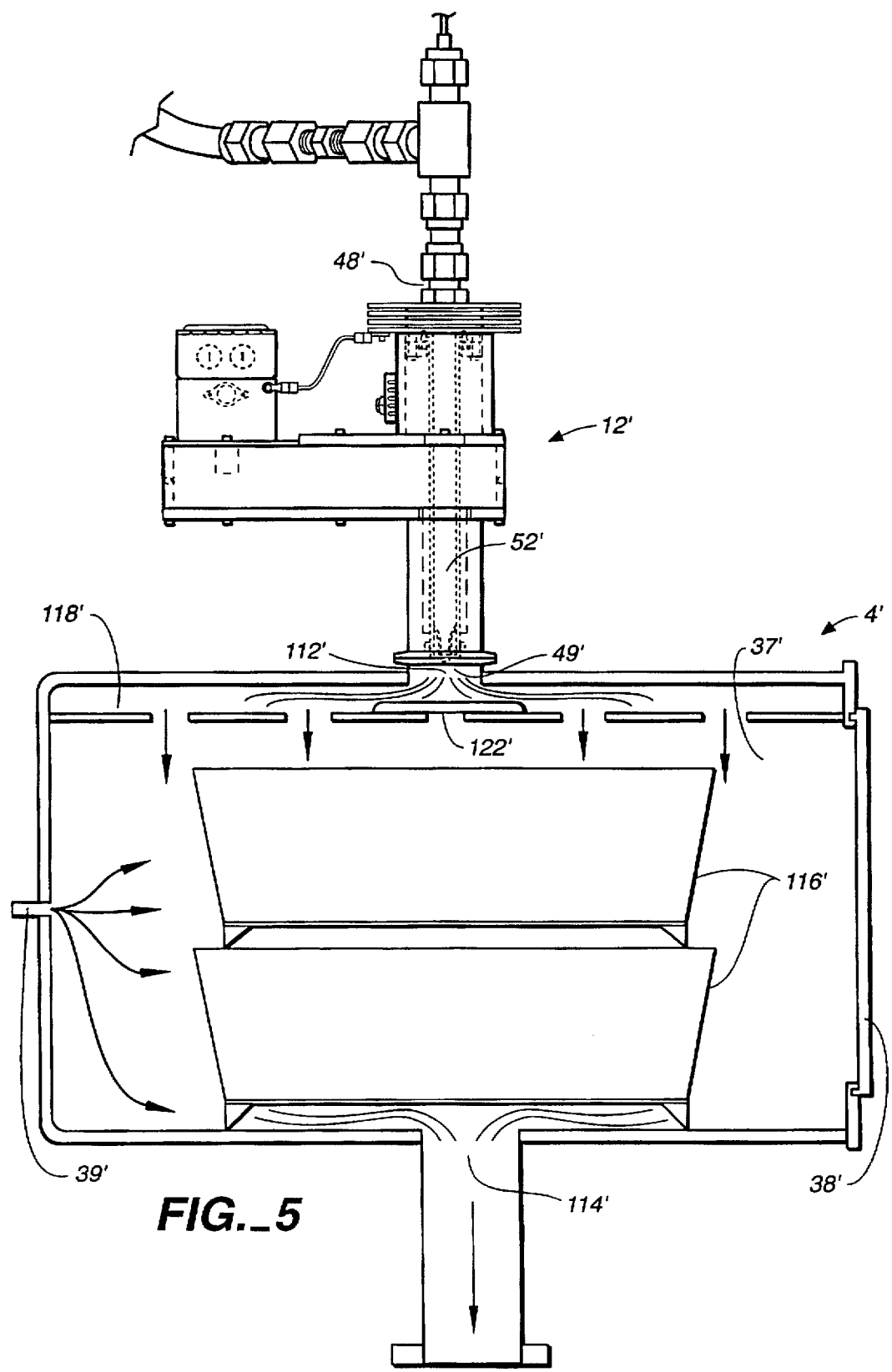
FIG._5

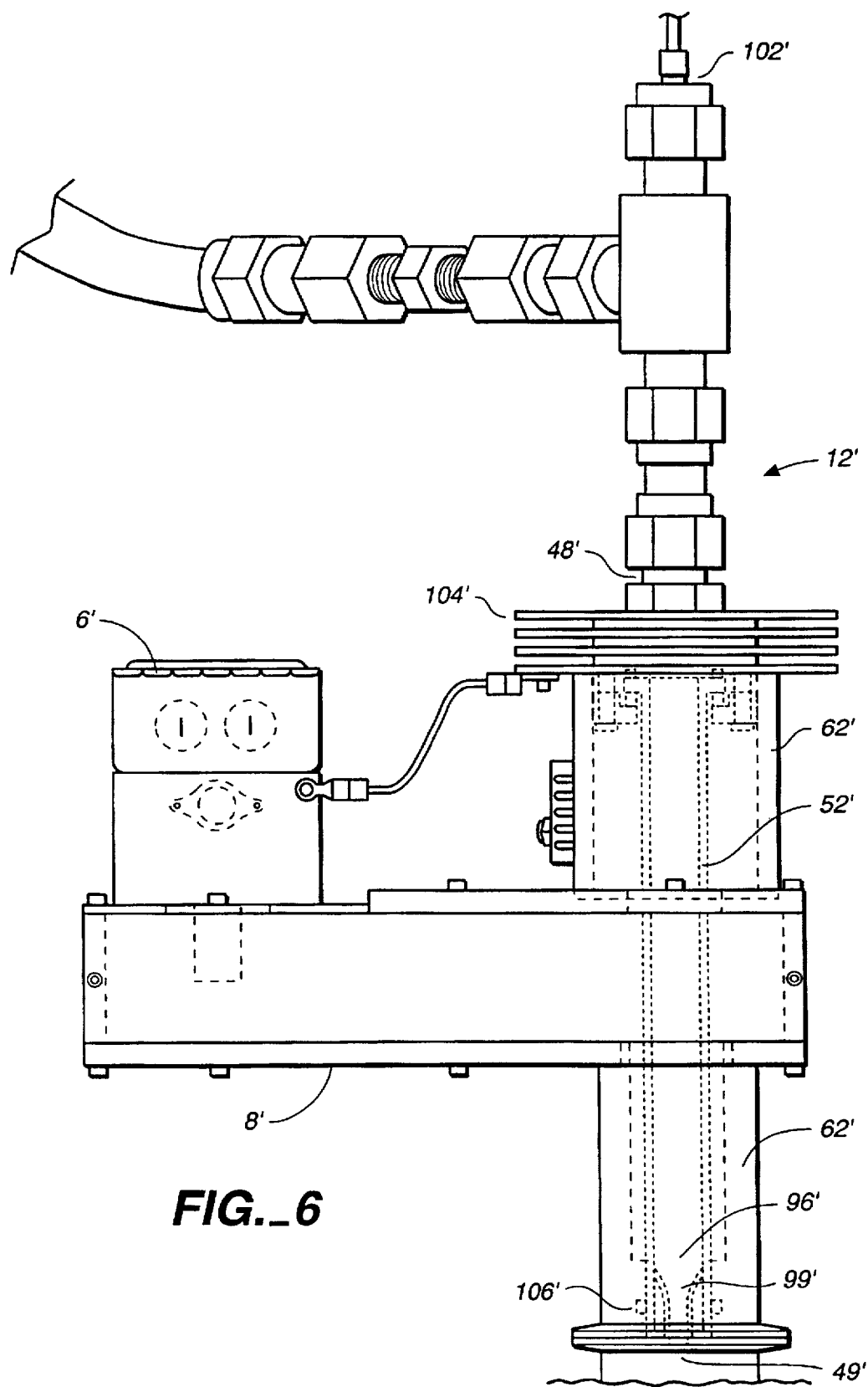
FIG._6

PLASMA WATER VAPOR STERILIZER APPARATUS

This is a division of application Ser. No. 08/491,170, filed Jun. 6, 1995, now U.S. Pat. 5,603,895, issued Feb. 18, 1997.

FIELD OF THE INVENTION

This invention relates to relatively low temperature sterilization of articles with gaseous species. In particular this invention relates to a method for sterilizing articles with neutral active species of a gas plasma generated from water vapor at temperatures below about 100° C.

BACKGROUND OF THE INVENTION

Methods using steam and disinfecting gases, particularly ethylene oxide, have been widely used for sterilizing medical products ranging from pharmaceutical preparations to surgical instruments.

A sterilizing method must effectively render all microbial organisms non-viable without damage to the article or goods being sterilized or its packaging. However, many disinfecting gases which meet this criteria, such as ethylene oxide, have been recognized to expose workers and the environment to safety hazards. Recent legislation has severely restricted the amount of hazardous gases such as ethylene oxide (a known carcinogen) in the working environment, or the use of any system or method which produces toxic residues or exhaust products. This has created a major crisis in hospitals and other areas of the health industry. Further, although steam sterilization is inexpensive and effective, it is too hot for many applications, particularly those involving sterilization of plastics with low melting points. Irradiation is a cooler process, but the large and expensive facilities required for irradiation are impractical for hospital uses.

The use of plasma in sterilizing methods has been suggested. Plasma is ionized or partially ionized gas which may be generated by the application of electromagnetic energy which may be obtained from different sources. The ionized gas will contact microorganisms on the surfaces of the items to be sterilized and effectively destroy the microorganisms.

Among the variety of gases attempted for use as sterilizing plasmas has been water vapor. However, these prior attempts have been reported as unsuccessful, or as being not particularly effective. Thus, U.S. Pat. No. 4,643,876, issued Feb. 17, 1987, inventors Jacobs and Lin, describes a plasma sterilization process and apparatus where the item to be sterilized has plasma generated around the item. Attempts to use a water plasma treatment by itself in this method of sterilization led to no significant sporicidal activity. Similarly, U.S. Pat. No. 3,701,628, issued Oct. 31, 1972, inventors Ashman, describes generating a plasma from sterilizing gas that is introduced into the sterilizing chamber. Plasmas formed of water vapor were reported as not being particularly effective.

U.S. Pat. No. 5,115,166, issued May 19, 1992, inventors Campbell and Moulton, describes the use of electrically neutral active species generated in a gas plasma to sterilize articles. In this system, articles to be sterilized are placed in a vacuum chamber which is attached to one or more plasma generators and a vacuum pump. The plasma generators use a source of microwave energy such as a magnetron to create the required electromagnetic field. The energy is conducted to the gas via a rectangular waveguide. The chamber is sealed and the vacuum pump is used to evacuate air from the chamber. Valves are then opened which allow gas to flow from a source container, through the plasma generators, through a gas distribution system, then through the sterilization chamber, and out through the vacuum pump. The gas mixture is usually oxygen, hydrogen, or a mixture of oxygen, hydrogen, and an inert gas. A strong electromagnetic field in the plasma generators interacts with the gases flowing through the plasma generators and generates a glow discharge. A variation of such an apparatus is described in U.S. Pat. No. 5,184,046, issued Feb. 2, 1993, inventor Campbell, where the plasma generators incorporate a cylindrical wave guide.

Both these apparatus of Patents '166 and '046 confine the electromagnetic field generating the plasma within the plasma generator. Once the gas flows out of the region with a high electromagnetic field, plasma is no longer created. Since highly reactive plasma components either react or decay quickly, relatively non-reactive components enter the sterilization chamber. Charged particles recombine in the gas distribution system to form electrically neutral components. Thus, the components entering the sterilization chamber include neutral active species which accomplish sterilization.

SUMMARY OF THE INVENTION

A method aspect of this invention for plasma sterilization comprises exposing an article to be sterilized in an evacuated sterilization chamber to the neutral active species of a plasma generated from water vapor where the electromagnetic field generating the plasma is confined to the plasma generator (which can be a plurality of plasma generators). The plasma-induced gas sterilization is preferably carried out at a temperature of less than about 100° C. and a pressure of from 0.1 to 150 torr, preferably about 0.1 to 40 torr.

Practice of the inventive method provides effective sterilization with the inexpensive and readily available water source and eliminates heavy, costly and potentially hazardous compressed gas cylinders as are necessary with many previously used sterilizing methods.

BRIEF DESCRIPTION OF THE DRAWINGS

FIG. 1 is a top view of a plasma sterilizer of this invention;

FIG. 2 is a cross-sectional view of the plasma sterilizer embodiment of FIG. 1;

FIG. 3 is a schematic illustration of a component of the FIG. 1 apparatus;

FIG. 4 is a cross-sectional view of another plasma sterilizer embodiment;

FIG. 5 is a side sectional view of the plasma sterilizer according to another embodiment of the invention; and, FIG. 6 is a detailed, sectional view of the plasma generator as a component of the plasma sterilizer shown in FIG. 5.

DETAILED DESCRIPTION OF THE INVENTION

Hospitals originally relied on disinfectants and steam autoclaves for sterilizing implements. In more recent years, ethylene oxide gas sterilization has made possible the sterilization of articles in heat sensitive packaging, thermolabile drugs, and heat sensitive medical supplies, and hospitals are highly dependent upon these procedures. However, ethylene oxide has been found to be a dangerous carcinogen and a number of new state laws protecting worker safety and the environment are restricting further use of ethylene oxide sterilizers in hospital environments. In addition, ethylene oxide is known to be a dangerous material from several other aspects. In its pure form it is explosive and flammable and therefore requires that all equipment must be so designed as to be classified as explosive proof. The most popular form of the diluted or explosive proof mixtures contains fluorocarbons (Freon), which are no longer environmentally acceptable. Also, because it is a carcinogen, state and federal authorities have imposed stringent regulations for the protection of workers and concerning emissions to the environment. This has placed further burdens and restrictions on the use of ethylene oxide sterilizers in all applications.

Gas sterilizers suitable for practicing this invention produce a plasma from a gas mixture consisting essentially of water vapor. The exhaust gas products of the gas mixture after use in the sterilization process fully satisfy current environmental and worker safety concerns, as the exhaust is almost entirely water vapor with traces of carbon dioxide and other gases arising from the interaction of plasma components with organic material in the articles being sterilized.

The plasma is produced as a result of applying an electric or electromagnetic field to the water vapor. The electromagnetic field can cover a broad frequency range, and can be produced by a magnetron, klystron, or RF coil. The present invention is usefully practiced with apparatus such as described by U.S. Pat. No. 5,115,166. In this system, articles to be sterilized are placed in a vacuum chamber which is attached to one or more plasma generators and a vacuum pump. The chamber is sealed and the vacuum pump is used to evacuate air from the chamber. Next, valves are opened which allow gas to flow from a source container, through the plasma generators, through a gas distribution system, through the sterilization chamber, and out through the vacuum pump. The gas is usually oxygen, hydrogen, or a mixture of oxygen, hydrogen, and an inert gas. Next, electrical power is supplied to circuitry which creates a strong electromagnetic field in the plasma generators. This field interacts with the gases flowing through the plasma generators and generates a glow discharge.

In the discharge, charged particles are accelerated by the field and gain kinetic energy. When these particles collide with other particles, energy transfer may result in the formation of more charged particles (ions and electrons) or excited atoms or molecules. Molecules may be broken into fragments such as atoms or radicals. The particles created in the collisions may also react with each other or with the feed gas to form yet more products. Light is also generated as particles in high energy states decay to lower energy states.

The apparatus is designed to confine the electromagnetic field which generates the plasma within the plasma generators. When the gas flows out of the plasma generators into the gas distribution system, where the field is vanishingly small, the acceleration of charged particles and the production of ions and electrons ceases. The most reactive of the components created in the discharge relax or react quickly, and the charged particles formed in the discharge recombine rapidly to form electrically neutral particles. The gas distribution system of the apparatus is designed so such recombination and relaxation processes will be essentially completed before the gas enters the sterilization chamber. Thus, relatively nonreactive components enter the sterilization chamber. These include the active species which accomplish sterilization. The active species are active in that they themselves, or other species formed by their interactions with other components present, can interact with microorganisms and inactivate them. However, the active species are not so reactive that they will be substantially depleted by reactions with or on surfaces they may encounter en route to a microorganism.

Plasma generation and sterilization are generally performed at reduced pressures, usually on the order of 0.1 to 100 torr. The lower end of the reduced pressure range is usually determined by the size (and cost) of the vacuum pump, whereas the upper end is usually determined by processing time considerations because the rate at which microbes are killed typically decreases as the pressure increases. It is possible that higher pressures could be used with more efficient plasma generators or with improved gas distribution systems. The vacuum pump is used to maintain these low pressures during the sterilization process. When the gas flows into the vacuum pump, it is compressed before being exhausted. The compression and concomitant heating accelerate the reactions of the active species to form innocuous compounds such that the pump's exhaust stream contains only nontoxic components.

The term "sterilization" connotes a process by which all viable forms of microorganisms are destroyed or removed from an object. In practice, it is impossible to make an absolute determination of the destruction or removal of microorganisms, so it has become customary to define sterility in terms of "probability of survivors." The practical goal of a sterilization process is therefore measured as a probability (e.g., $10^{-3}$, $10^{-6}$, $10^{-12}$), the probability indicating the lethal effect of a particular sterilizing dose or regimen. It is usual to assume increased time of exposure to a set of sterilizing conditions will decrease the probability of survivors accordingly. Doubling the sterilizing time of identical conditions would result in a squaring of the probability term, for example $10^{-6}$ would become $10^{-12}$.

Broadly, the present invention can be viewed as essentially requiring a plasma generator, a sterilizing chamber, and a source of water vapor in fluid communication with the plasma generator. Although particularly preferred apparatus for practicing the invention is illustrated by U.S. Pat. No. 5,115,166 (and by U.S. Pat. No. 5,184,046), the disclosures of which are incorporated herein by reference, it should be understood that variations in the preferred apparatus components are within the scope of this invention. For example, U.S. Pat. No. 5,244,629, issued Sep. 14, 1993, the disclosure of which is incorporated by reference, describes a sterilization treatment in which the article to be sterilized is alternatively exposed to an anti-microbial agent and to the neutral active species of a gas plasma.

Turning to FIG. 1, a top view of a first plasma sterilizer embodiment suitable for use with this invention is illustrated. The plasma sterilizer has one or more means for generating plasma 2 (as illustrated by this embodiment, there are three plasma generating tubes 10, 12, 14) and a sterilizing chamber 4. The plasma generating means 2 comprises an electromagnetic field generator, such as a magnetron 6 and a waveguide 8 which directs the electromagnetic field. This gas plasma is generated from the water vapor, as is hereinafter further described and exemplified.

The water vapor, which is the plasma source gas, is directed into plasma generating tubes 10, 12, and 14 by gas delivery lines 16, 18, and 20 leading from the flow controller 22. The operation of flow controller 22 is controlled by a central processing unit (CPU) 28 by standard procedures. Flow controller 22 and CPU 28 can be any of the conventional, standard devices used for gas flow control in plasma generating equipment.

The water vapor can originate from water reservoir 24, which is in fluid communication with the flow controller 22.

It is important to prevent condensation of the vapor in the piping between the water reservoir 24 and the inlets 26, 16, 18, and 20 to the means for plasma generation 2. Condensation prevention is well known to persons skilled in the art, and typically simply requires that the temperature in the piping is kept high enough to maintain the vapor pressure in the piping along the fluid flow path.

Water vapor may be generated by various methods. For example, liquid water can be flowed from a source through a metering valve and into a vaporizer. In the vaporizer, water can be flowed over heated surfaces and evaporated, with the water vapor then being flowed into the plasma generators. Alternatively, the flow of water vapor itself can be regulated, as illustrated by the above described embodiments.

The sterilizing chamber 4 may comprise top plate 30, side plates 32 and 34, bottom plate 36 (not shown), back plate 37, and front sealing door 38 through which articles or materials to be sterilized are placed in the chamber. The plates are shown attached together in a sealed relationship to form a vacuum chamber, such as by welding. The door 38 is secured in a sealed relationship with the sterilizing chamber.

Thus, plasma generation occurs in one chamber, and the activated gas is then fed via an indirect passageway to the sterilizing chamber. This indirect passageway is of a construction sufficient to prevent direct impingement of nascent plasma generated in the plasma generating chamber onto the article being sterilized. This indirect passageway may be constructed from a restrictor and a plasma distributor.

The plates and door of the sterilizing chamber can be made of any material having the strength required to withstand the external atmospheric pressure when the chamber is evacuated. Stainless steel or aluminum plates and door can be used. The internal surface material of the chamber may affect the concentration(s) of killing species available in the chamber. One useful material is pure (98%) aluminum which can be applied either as a liner or as a flame-sprayed coating on all internal walls of the stainless steel chamber. An alternate material is nickel. However, we prefer to coat the chamber interior with an inert polymer coating (e.g. PTFE).

The gases are exhausted from the sterilizing chamber through exhaust outlet port 42 to a conventional vacuum pump system (not shown).

FIG. 2 is a top cross-sectional view of the plasma sterilizer embodiment of FIG. 1. Each of the plasma generators 10, 12, and 14 comprise an inlet cap 44 with a gas inlet port 48 leading to a respective plasma generator tube 51, 52, or 53 leading through the waveguide 8. In the waveguide 8, the water vapor in tubes 51, 51, and 53 is energized and converted to a plasma.

The plasma generator tube directs the plasma flow into the gas distribution tubes 54, 56, and 58 from which the plasma is fed into the evacuated sterilizing chamber 60. The preferred plasma generating tubes and plasma distributing tubes are made of quartz. However, any other materials with the necessary physical, chemical, and electrical properties for plasma generation in an electromagnetic field can be used for the plasma generating tubes. Similarly, the conduits and tubing used for transport of plasma from the plasma generator to the sterilizing chamber can be any solid material which has the requisite shape and strength and which is resistant to chemical action and degradation by the plasma gases. Suitable transport conduit materials include quartz and other plasma corrosion resistant glasses, stainless steel and other oxidation resistant metals, and oxidation resistant plastics such as fluorocarbon polymers, e.g. PTFE and the like, and siloxane polymers.

In a particularly preferred embodiment the plasma is fed into a plenum portion of chamber 60, with the plenum defined by a perforated lower plenum plate, or baffle plate (not illustrated). The plenum plate can be made of any of the materials used for constructing the sterilizing chamber 60, with PTFE coating on metal being a preferred embodiment. The size, number, and placement of the perforations in the plenum plate may vary. The size and distribution of holes in the plate should provide sufficiently uniform gas flow through the sterilization chamber and may also be chosen to keep residual electromagnetic energy from entering the sterilization chamber.

The plasma generator tubes are enclosed in tubular metal cooling tubes 62 and 64. The caps 44 and the cooling tubes 62 and 64 are preferably provided with groves or cooling fins (not shown) in a conventional manner to increase their efficiency in removing heat from plasma generator tubes. The length and inner diameter of the cooling tubes are chosen to attenuate the electromagnetic field in the waveguide to keep microwave energy from entering the gas distributor and sterilization chamber. As a consequence, the only places where the field is strong enough to generate a plasma are within the plasma generating tubes in regions within or near the waveguide. The distal ends of the gas distribution tubes 54, 56, and 58 are supported by spring-biased end supports 66 mounted on sideplate 32, but could be modified for gas distributor plenum designs, as known in the art.

The door 38 is held in sealing engagement by atmospheric pressure against the O-ring seal 40 mounted in the flange 41 extending from the side plates 32 and 34, and the top and bottom plates 30 and 36 (not shown). Optionally, additional conventional closure clamp or latch devices can be used to insure closure of the door before chamber evacuation is initiated.

Turning to FIG. 3, a schematic detail of a water reservoir 24 is illustrated, as was used for experiments hereinafter more fully described. A container 70 capable of withstanding vacuum was partially filled with distilled or deionized water. A thermocouple 72 and an electric heater 74 were immersed in the water. The thermocouple 72 and heater 74 were connected to a control unit (not illustrated) which regulated electrical power to the heater to maintain the temperature of the water at 50° C. The container 70 was placed in an insulated chamber which was held at 50° C. A tube ran from the container to the flow controller 22 in a second chamber, which was held at 60° C. A condensation trap 76 was placed in the line between the flow controller 22 and the container 70 to prevent any condensation from reaching the flow controller 22. A three-way valve 25 was inserted in the line between the trap 76 and the flow controller 22 to allow vacuum to be applied directly to the upstream side of the flow controller 22 to aid in removing any accumulated condensation during maintenance operations. The flow controller 22 need not be electronic, but could be a variety of flow control means, such as a needle valve, and the trap 76 is preferred but optional.

The embodiment described above has been presented with three plasma generating units. The number of generating units is not critical, being selected to provide a good plasma distribution in the particular sterilizing chamber used. Any desired number of plasma generators can be used with each sterilizing chamber and are intended to be included within the scope of this invention. It will be also be readily apparent that any number of gas plasma tubes can be positioned to interact with the electromagnetic field generated from a single magnetron and that various waveguide configurations can be used to achieve this effect.

Turning to FIG. 5, a side sectional view of the plasma sterilizer according to another embodiment of the invention is illustrated. The plasma sterilizer comprises one or more plasma generators 12' connected to a sterilizing chamber 4'. In a preferred embodiment, there are three plasma generators mounted on top of the sterilizing chamber to provide a uniform and adequate distribution of sterilizing gas mixture into the sterilizing chamber.

FIG. 6 is a detailed, sectional view of the plasma generator. Each plasma generator 12' comprises a housing 62' that is mounted onto a top portion of the sterilizing chamber. The housing supports a plasma generator tube 52' that is preferably a quartz tube transparent to microwave. One end of the plasma generator tube 52' is coupled to a gas inlet 48' for receiving a gas or gas mixture from outside the housing 62'. The other end of the plasma generator tube is coupled to an outlet manifold 49' at the bottom of the housing that allows the gas mixture to flow from the generator tube to the sterilizing chamber 4'.

The housing 62' also supports a waveguide 8', a portion of which intersects the plasma generator tube 52'. The waveguide serves to transmit microwave energy from a microwave source, such as a magnetron 6', to the portion of the plasma generator tube inside the waveguide. Typically, the plasma generator tube is positioned at a crest of the standing waves in the waveguide. The initiation of the plasma is facilitated by a striker 102' near the gas inlet. The striker is connected to a high voltage source (not shown). In this way, the gas mixture that flows through the plasma generator tube is energized in the waveguide and converted into a plasma.

The housing 62' and the waveguide 8' assembly are preferably constructed out of a good conductor such as aluminum and designed to minimize microwave leakage outside the assembly. The housing is also able to establish good thermal contact with the plasma generator tube so that it can dissipate heat generated in the plasma. In a preferred embodiment, cooling fins 104' near the top portion of the housing help to improve heat dissipation.

As the gas mixture flows through the generator tube it is converted into a nascent plasma. It then exits via the outlet manifold into the sterilizing chamber. During that passage the nascent plasma is transformed into a cooler gas mixture of essentially neutral species. The conversion is facilitated by routing the gas mixture through a restrictor 99' and the outlet manifold 49'.

The restrictor 99' helps to define the plasma generating tube 52' as a plasma generating chamber distinct from the sterilizing chamber 4'. In a preferred embodiment, the restrictor is formed by a special termination of the plasma generator tube. Near the outlet manifold 49', the generator tube is formed into a dual-wall tube, with the inner tube terminating into a smooth surfaced venturi restriction 96' of reduced cross-sectional area. The outer wall has the same cross-sectional area as the rest of the generator tube. An O-ring 106' around the dual wall portion secures the plasma generator tube in sealed engagement with the housing near the outlet manifold. The dual-wall construction has the advantage of insulating the O-ring from the heat of the plasma flowing in the inner tube.

The restrictor 99', by virtue of its reduced aperture, serves several important functions. First, different optimal pressures can be maintained in the two different chambers. Typically, the plasma generating chamber is maintained at a higher pressure than the sterilizing chamber, the former being optimized for plasma generation and sustenance and the latter being optimized for uniform dispersion of the sterilizing gas. Secondly, and especially in combination with the outlet manifold, the restrictor increases the probability of plasma components colliding into a surface. This physical structure thus promotes the conversion or recombination of charged particles in the plasma into neutral species. Thirdly, harmful ultra-violet ("UV") radiation generated in the plasma in the generator tube only has a small opening through which to escape into the sterilizing chamber.

Referring back to FIG. 5, the sterilizing chamber 4' comprises a sterilizing enclosure 37' with a sealing door 38'. An inlet port 112' at the top of the enclosure is coupled to the outlet manifold 49' of the plasma generator. An exhaust port 114' at the bottom of the sterilizing enclosure is coupled to an external vacuum pump system (not shown). The articles to be sterilized may be placed in baskets 116' inside the sterilizing enclosure. Alternatively, a perforated exhaust panel may be mounted across the enclosure and above the exhaust port to form a platform for supporting articles to be sterilized. Near the top of the sterilizing enclosure and below the inlet port 112', a perforated gas distribution panel 118' is mounted to distribute the gas mixture including the neutral species entering through the inlet port 112' uniformly throughout the sterilizing enclosure. The perforated gas distribution panel is preferably made of rigid and inert material, such as PTFE, tempered glass, stainless steel or stainless steel coated with PTFE. Furthermore, the material should be opaque to UV light. In general, the perforated gas distribution panel 118' should comprise a self-supporting structure, the main function of which is to distribute the in-flowing gas mixture in a uniform manner into the sterilizing enclosure 37'. In this embodiment, the structure from the base of the plasma generator tube 52' to the perforated gas distribution panel 118' can be regarded as forming the outlet manifold 49'.

A second inlet port 39' on a side wall of the sterilizing enclosure allows antimicrobial additives to be introduced as a vapor or liquid from an external source (not shown).

During operation of the plasma sterilizer, the nascent plasma generated in the plasma generating tube 52' emerges via the outlet manifold 49' into the sterilizing chamber 4'. As described before, virtually all of the charged particles generated in the plasma are converted into neutral species as they pass through the restrictor 99' and the outlet manifold 49' (see also FIG. 6). Similarly, the UV radiation generated in the plasma is greatly reduced by the restrictor 99' and the outlet manifold 49'. Thereafter, the gas mixture is made to negotiate through the perforated gas distribution panel 118' before it enters the sterilizing chamber 4' and acts on the article 120' to be sterilized. In a preferred embodiment a disk 122' made of inert material such as PTFE or glass is placed on the top surface of the perforated gas panel directly below the inlet port 112'. The perforated gas distribution plate, especially in combination with the disk 112', serves several functions. Primarily, it cools and disperses the gas mixture uniformly in the sterilizing enclosure. Secondly, it helps to block what little remaining UV radiation that may have been admitted into the outlet manifold 49'. Finally, it provides an additional surface for conversion of the few remaining charged particles in the gas mixture to neutral species. In this manner, by the time the gas mixture reaches the article to be sterilized, the main sterilizing agent contained therein is essentially neutral species generally devoid of undesirable charged particles and UV radiation.

The apparatus of this invention generates a sterilizing species derived from water vapor, as exemplified hereinafter. The sterilization is carried out in the sterilization chamber at a vacuum pressure of from about 0.1 to 150 torr and preferably from about 0.1 to about 40 torr. The temperature in the sterilizing chamber is maintained below 100° C., and preferably is from about 35° C. to about 82° C. Under these conditions, effective sterilization is effected without significant deterioration of packaging materials in which articles to be sterilized may be placed.

The method of this invention for plasma sterilization comprises exposing an article to be sterilized to a plasma generated from water vapor at temperatures of less than 100° C., a pressure of from 0.1 to 150 torr, and an effective treatment time. The treatment time efficacy will vary depending on the article being sterilized, whether or not it is wrapped or packaged, and the type of wrap or packaging. For instance, articles with no lumens or no relatively inaccessible features can be sterilized more rapidly than those articles with lumens. Articles with several layers of wrapping may require more time than those with a single layer of wrapping. Effective treatment times may be determined empirically.

In an optimum method of sterilizing, the articles to be sterilized are placed in the sterilizing chamber, supported in conventional fixtures (e.g. wire baskets) which permit the activated gas to reach all surfaces of the articles. The chamber is closed, the sterilizing chamber is evacuated, plasma generation is initiated, and the activated gas is directed into and through the sterilizing chamber.

When the activated gas is compressed and heated in the vacuum pump, the activated species in the gas react very quickly to form non-toxic gases which may be exhausted with minimal treatment.

Plasma sterilization apparatuses of the invention are readily adapted to perform other sterilizing cycles in addition to plasma sterilization, particularly such as steam sterilization (autoclaving).

With reference to FIG. 4, another embodiment 100 of the invention is schematically illustrated where a means for plasma generation 102 is in communication with sterilizing chamber 104 with valve 103 interposed so as to control communication of plasma generated in the plasma generator 102 from the sterilizing chamber 104. The source of the water vapor is water reservoir 124. Water flows into heater 126 and is converted into water vapor. Heater 126 is controlled by temperature controller 156. Water vapor then flows through valve 130, flow controller 122, and into plasma generator 102, where it is converted into a plasma. The activated gas then flows through valve 103, through sterilizing chamber 104, through valve 132, and out through vacuum pump 140. Alternatively, steam can be generated by adjusting heater 126 to heat the water to a much higher temperature. Steam would then flow through valve 128 into chamber 104, with valves 103 and 130 closed.

Still with reference to FIG. 4, in operation of this embodiment as a steam autoclave, valves 103, 128, 130, 132, 134, and 148 would be initially closed. An article to be sterilized 136 would be loaded into chamber 104 and the door 138 closed and sealed. One could, if desired, open valve 132 to evacuate air from the chamber 104 through vacuum pump 140 while monitoring chamber pressure on gauge 142. Then valve 132 would be closed and valve 128 and 134 would be opened. Steam generated by heater 126, adjusted to an appropriate temperature by controller 156, would flow through valve 128 and into the sterilizing chamber 104. The temperature of the system would be monitored by sensor 144 in the drain line 158, and thermostat valve 146 would regulate the temperature (and pressure) of steam in the system. After a prescribed time, valves 128 and 134 would be closed and valve 132 would be opened. Steam would be evacuated from the sterilizing chamber 104 through vacuum pump 140. Then valve 132 would close, valve 148 would open, and the chamber would be brought to atmospheric pressure with sterile air. Door 138 would be opened and the sterilized article 136 would be removed.

In the operation of this embodiment as a plasma sterilizer, valves 103, 128, 130, 132, 134, and 148 would be initially closed. An article to be sterilized 136 would be loaded into chamber 104 and the door 138 would be closed and sealed. Valves 103 and 132 would then be opened and air would be evacuated from the sterilizing chamber 104 and the plasma generator 102 through vacuum pump 140. Then valve 130 would open and the plasma generator 102 would be activated. Water vapor generated by heater 126, adjusted to an appropriate temperature by controller 156, would flow through valve 130 and flow controller 122 into plasma generator 102, where it would be converted into a plasma. The activated gas would flow through valve 103 into a gas distribution manifold 154, through the sterilizing chamber 104, and out through valve 132 and vacuum pump 140. After a prescribed period of time, valve 130 would be closed, the plasma generator 102 would be turned off, and remaining gases would be pumped out of the sterilizing chamber and plasma generator. Then valves 132 and 103 would be closed. Valve 148 would open, and the chamber would be brought to atmospheric pressure with sterile air. Door 138 would be opened and the sterilized article 136 would be removed.

Such a multiple function sterilizing apparatus 100 provides increased operating flexibility since plasma sterilization or steam sterilization can be accomplished with the same apparatus.

EXAMPLE 1

Biological indicators are characterized preparations of specific microorganisms resistant to a particular sterilization process. They are used to assist in the qualification of the physical operation of sterilization apparatus and to validate a sterilization process for a particular article. In this example, the biological indicators were *Bacillus circulans* spores inoculated onto filter paper carriers and sealed in pouches made of porous polyethylene (Tyvek) and Mylar. Packages for the biological indicators were obtained from Baxter Laboratories as "Plastipeel Pouches." Filter paper disks (¼ inch diameter Schleicher & Schuell 740E) were used as carriers for spores. Each disk was inoculated with about $2 \times 10^6$ spores of *B. circulans*.

The biological indicators were placed into the sterilizer apparatus and exposed to a plasma cycle. During the plasma cycle, water vapor was flowing at a rate of about 0.8 standard L/min. The sterilization chamber pressure was about 0.2 torr.

After exposing the biological indicators to the sterilizing water vapor treatment for 78 minutes, the indicators were removed and tested for sterility.

The paper disks were aseptically transferred into growth medium (tryptic soy broth) and incubated at 37° C. for 7 days. No growth was observed, indicating that all the bacteria spores on the disks were inactivated.

EXAMPLE 2

Three pieces of 14 gauge stainless steel tubing were inoculated with about $2 \times 10^5$ *B. circulans* spores each. Each piece was placed in the center of a length of polyvinyl chloride tubing 1.8 m long and 1.27 mm ID (Tygon tubing, made by Norton Performance Plastics Corp.). Each piece of PVC tubing was coiled and sealed in a Tyvek/Mylar sterilization pouch, as described in Example 1. The three assemblies were placed in the sterilizer and treated for six hours. The inoculated stainless steel pieces were recovered, transferred into growth medium, and incubated for three days. No growth was observed.

EXAMPLE 3

The plasma sterilization system was equipped with a temperature control system which caused the electrical power to the magnetrons to be interrupted when a thermocouple in the sterilization chamber reached a temperature of 180° F. The power was restored when the temperature dropped to about 177° F. This modification is similar to the one put forth in U.S. Pat. No. 5,186,893, issued Feb. 16, 1993.

The tests were run twice. Between the tests, a slight modification was made to the exhaust line between the sterilizing chamber and the vacuum pump. As a result, the pressure in the sterilizing chamber for the second test was slightly higher than for the first (200 mTorr v. 170 mTorr).

The articles sterilized were "test packs" similar (but not identical) to those used to qualify ethylene oxide sterilization processes. The packs were constructed as follows: Disks of filter paper about 5 mm in diameter were inoculated with about 2×10$^6$ *Bacillus circulans* spores. Ten disks were placed in two Tyvek/Mylar sterilization pouches (five disks per pouch) and the pouches were sealed using a heat sealer. Each pouch was placed in the barrel of a plastic 20 cc syringe with the Tyvek side facing the inside of the syringe barrel. The syringe plungers were inserted but did not touch the pouches. There were no tip caps on the ends of the syringes. The syringes were placed in the center of a stack of two Huck towels. (A "Huck" towel is a woven cotton towel commonly used in hospital procedures.) An oral airway was placed on one side of the syringes and a 10 inch piece of latex tubing was placed on the other side of the syringes. Two more Huck towels were placed on the instruments. This stack was then wrapped in two pieces of cotton/polyester sterilization wrapping material, 27 in. by 27 in. each.

The pack was placed in the sterilization chamber and the thermocouple was placed under the top fold of the outermost wrapper. The chamber was sealed and the vacuum pump was activated. The chamber was evacuated for about 20 minutes to allow this rather absorptive load to outgas. The water vapor flow was started and the plasma was initiated. The treatment lasted for four hours in all. The thermocouple reached its setpoint (180° F.) about 85 minutes after the plasma was started; in all, the plasma was on about 185 minutes during the four hour exposure.

After exposure, the packs were disassembled and the disks were transferred into growth medium. No growth was observed after either test.

It is to be understood that while the invention has been described above in conjunction with preferred specific embodiments, the description and examples are intended to illustrate and not limit the scope of the invention, which is defined by the scope of the appended claims.

It is claimed:

1. An apparatus for plasma sterilization of articles comprising:
   a sterilizing chamber and a plasma generator, the plasma generator including (a) a source of water vapor, (b) an inlet for receiving the water vapor from the source, (c) a plasma generating chamber for generating plasma from the water vapor and in communication with the inlet means, and (d) an outlet for communicating with the sterilizing chamber, the source of water vapor including a heater to maintain a predetermined temperature.

2. The apparatus for plasma sterilization as in claim 1 further including means for performing steam sterilization in the sterilizing chamber.

3. A dual function sterilizing apparatus comprising:
   a sterilizing chamber;
   plasma generating means for generating a plasma and being associated with the chamber;
   steam sterilizing means for generating steam and being associated with the chamber; and,
   fluid control means for placing either plasma or steam in communication with the sterilizing chamber.

* * * * *